(12) United States Patent
Phillips

(10) Patent No.: US 6,726,637 B2
(45) Date of Patent: Apr. 27, 2004

(54) BREATH COLLECTION APPARATUS

(76) Inventor: Michael Phillips, 1 Horizon Rd., Apt. 1415, Fort Lee, NJ (US) 07024

( * ) Notice: Subject to any disclaimer, the term of this patent is extended or adjusted under 35 U.S.C. 154(b) by 0 days.

(21) Appl. No.: 10/008,642

(22) Filed: Dec. 6, 2001

(65) Prior Publication Data

US 2003/0109794 A1 Jun. 12, 2003

(51) Int. Cl.$^7$ .............................. A61B 5/08; B65D 81/00
(52) U.S. Cl. ....................... 600/543; 600/529; 600/532; 73/23.3
(58) Field of Search ....................... 600/529, 532–543; 73/23.3

(56) References Cited

U.S. PATENT DOCUMENTS

| | | | |
|---|---|---|---|
| 5,284,054 A | * 2/1994 | Loebach | 73/23.3 |
| 5,465,728 A | 11/1995 | Phillips | 128/730 |
| 5,479,815 A | * 1/1996 | White et al. | 73/23.3 |
| 5,848,975 A | 12/1998 | Phillips | 600/532 |
| 5,996,586 A | 12/1999 | Phillips | 128/898 |
| 6,033,368 A | * 3/2000 | Gaston, IV et al. | 600/532 |
| 6,221,026 B1 | 4/2001 | Phillips | 600/532 |
| 6,254,547 B1 | 7/2001 | Phillips | 600/532 |
| 6,374,662 B1 | * 4/2002 | Oda et al. | 73/23.34 |
| 6,467,333 B2 | * 10/2002 | Lewis et al. | 73/31.05 |

OTHER PUBLICATIONS

Phillips M. and Greenberg J. "Method for the collection and analysis of volatile compounds in the breath" Journal of Chromatography Biomedical Applications 1991; 564(1) 242–249.

Phillips M. and Greenberg J. "Ion–trap detection of volatile organic compounds in alveolar breath" Clinical Chemistry 1992; 38(1): 60–66.

Phillips M. "Breath tests in medicine" Scientific American 1992; 267(1): 74–79.

Phillips M. "Detection of carbon disulfide in breath and air: A possible new risk factor for coronary artery disease" International Archives of Occupational and Environmental Health 1991; 64:119–123.

Phillips M., Sabas M. and Greenberg J. "Increased pentane and carbon disulfide in the breath of patients with schizophrenia" Journal of Clinical Pathology 1993; 46: 861–864.

Phillips M., Sabas M. and Greenberg J. "Alveolar gradient of pentane in normal human breath" Free Radical Research Communications 1994; 20(5): 333–337.

Phillips M., Greenberg J. and Awad J. "Metabolic and environmental origins of volatile organic compounds in breath" Journal of Clinical Pathology 1994; 47: 1052–1053.

Phillips M. Erickson GA., Sabas M., Smith JP. and Greenberg J. "Volatile organic compounds in the breath of patients with schizophrenia" Journal of Clinical Pathology 1995; 48: 466–469.

Phillips M. "Method for the collection and assay of volatile organic compounds in breath" Analytical Biochemistry 1997; 247: 272–278.

Phillips M., Gleeson K., Hughes JMB., Greenberg J. and Cataneo RN. "Variation in volatile organic compounds in the breath of normal humans" Journal of Chromatography B 1999; 720: 75–88.

(List continued on next page.)

Primary Examiner—Robert L. Nasser
Assistant Examiner—Patricia Mallari
(74) Attorney, Agent, or Firm—Pitney, Hardin, Kipp & Szuch LLP

(57) ABSTRACT

An arrangement for the collection, concentration, and optional analysis of volatile organic components in alveolar breath includes a condensation unit which removes water vapor from the alveolar breath.

6 Claims, 2 Drawing Sheets

OTHER PUBLICATIONS

Phillips M., Greenberg J. and Cataneo RN. "Effect of age on the profile of alkanes in normal human breath" Free Radical Research 2000; 33: 57–63.

Phillips M., Cataneo RN., Greenberg J., Gunawardena R., Naidu A. and Rahbari–Oskoui F. "Effect of age on the breath methylated alkane contour, a display of apparent new markers of oxidative stress" Journal of Laboratory and Clinical Medicine 2000: 136: 243–9.

Phillips M., Brand DA., Cataneo RN., Cummin ARC., Gagliardi AJ., Gleeson K., Greenberg J., Maxfield RA. and Rom WN. "Detection of lung cancer with volatile markers in the breath" (submitted publication).

Phillips M., Gleeson K., Hughes JMB., Greenberg J., Cataneo RN. and Baker L. "Volatile organic compounds in breath as markers of lung cancer: a cross–sectional study" Lancet 1999; 353: 1930–1933.

* cited by examiner

BREATH COLLECTION APPARATUS

FIELD OF THE INVENTION

The invention relates to an improved arrangement for the collection and analysis of alveolar breath. Surprisingly it has been found that by condensing water vapor present in a breath sample, enhanced detection of volatile organic components is achieved.

BACKGROUND OF THE INVENTION

Normal mammalian breath, including human alveolar breath contains a large number of volatile organic compounds in low concentrations (nanomolar or picomolar). Many of these compounds originate from the capillary blood; they enter the alveoli of the lungs by diffusion across the pulmonary alveolar membrane. Therefore, the analysis of breath opens a unique window onto the composition of the blood.

The collection and analysis of the breath presents several technical difficulties, but may yield information of considerable medical interest. There is evidence that the composition of alveolar breath may be altered in several disorders, including lung cancer, liver disease, inflammatory bowel disease, rheumatoid arthritis, heart transplant rejection, renal failure and schizophrenia. The chemical analysis of breath therefore provides a non-invasive diagnostic test for the diagnosis of these and other diseases as set forth in the following publications and patents, all of which are incorporated by reference herein; Phillips M and Greenberg J: A method for the collection and analysis of volatile compounds in the breath. Journal of Chromatography. Biomedical Applications 1991; 564(1):242–249; Phillips M and Greenberg J: Ion-trap detection of volatile organic compounds in alveolar breath. Clinical Chemistry 1992; 38(1): 60–66; Phillips M: Breath tests in medicine. Scientific American 1992; 267(1):74–79; Phillips M: Detection of carbon disulfide in breath and air: A possible new risk factor for coronary artery disease. International Archives of Occupational and Environmental Health 1992; 64:119–123; Phillips M, Sabas M and Greenberg J: Increased pentane and carbon disulfide in the breath of patients with schizophrenia. Journal of Clinical Pathology 1993; 46:861–864; Phillips M, Sabas M and Greenberg J: Alveolar gradient of pentane in normal human breath. Free Radical Research Communications 1994; 20(5):333–337; Phillips M, Greenberg J and Awad J: Metabolic and environmental origins of volatile organic compounds in breath. Journal of Clinical Pathology 1994; 47:1052–1053; Phillips M, Erickson G A, Sabas M, Smith J P and Greenberg J: Volatile organic compounds in the breath of patients with schizophrenia. Journal of Clinical Pathology 1995; 48:466–469; Phillips M: Method for the collection and assay of volatile organic compounds in breath. Analytical Biochemistry 1997; 247:272–278; Phillips M, Gleeson K, Hughes J M B, Greenberg J, Cataneo R N, Baker L and McVay W P: Detection of volatile markers of lung cancer in alveolar breath. Lancet 1999; 353:1930–33; Phillips M, Herrera J, Krishnan S, Zain M, Greenberg J and Cataneo R N: Variation in volatile organic compounds in the breath of normal humans. Journal of Chromatography B 1999; 729:75–88; Phillips M, Greenberg J and Cataneo RN: Effect of age on the profile of alkanes in normal human breath. Free Radical Research 2000; 33:57–63; Phillips M, Cataneo R N, Greenberg J, Gunawardena R, Naidu A and Rahbari-Oskoui F: Effect of age on the breath methylated alkane contour, a display of apparent new markers of oxidative stress. Journal of Laboratory and Clinical Medicine 2000:136:243–9.

The major technical difficulties in chemical analysis of breath arise from:

(1) the large numbers of volatile organic compounds (possibly 200 or more) found in breath and necessitating separation prior to assay (e.g.; by gas chromatography combined with mass spectroscopy) (GC/MS), and (2) the very low concentration of the compounds, which are below the limits of sensitivity of currently available GC/MS instruments, therefore necessitating concentration of the breath prior to analysis.

The above-described difficulties may be circumvented by the use of a breath collecting apparatus which collects and concentrates the breath into a sample suitable for assay by GC/MS. However, the design and operation of an effective breath collecting apparatus presents a number of technical requirements:

(1) Subject comfort: the apparatus should present no significant resistance to exhalation (which might cause discomfort for the subject providing a breath sample).

(2) Subject safety: the apparatus should provide no hazard to the subject, such as exposure to potential sources of inhaled infectious microorganisms.

(3) Freedom from contamination: the apparatus should not incorporate any structural components such as plastics and adhesives containing volatile organic compounds which continuously out gas, causing contamination of the sample.

(4) Alveolar sampling: normal mammalian breath contains two components: the "dead space" breath originating from the pharynx, trachea and bronchial tree where no gaseous interchange occurs, and alveolar breath from the alveoli of the lungs which contains the volatile organic compounds of interest which have diffused from the blood. The sample should be drawn principally from alveolar breath, not dead space breath.

(5) Site of use: The arrangement should be transportable to the site of use, for example, a patient's bedside in a hospital or the point of use in the field.

(6) Concentration of sample: The ultimate purpose of the apparatus is to concentrate volatile organic compounds in the alveolar breath, while allowing the nitrogen, oxygen, and carbon dioxide in the breath to escape unhindered. The commonest concentration techniques are cryogenic (i.e.; capture in a cold trap), adsorptive (i.e.; capture in a trap containing an adsorptive resin or some other binding agent) or chemical (i.e.; capture by interaction with a chemical compound).

Unfortunately, mammalian breath is saturated with water vapor, which frequently interferes with the concentration and/or analysis of the volatile organic compounds of interest in the alveolar breath. Water vapor condenses onto cool surfaces. This may potentially result in partitioning of volatile organic compounds in the gaseous phase into the aqueous phase, with a consequent depletion of volatile organic compounds in the analyzed specimen.

Consequently, arrangements for the collection of alveolar breath such as described in U.S. Pat. No. 5,465,728, which is incorporated by reference herein, have typically required the use of heating systems in order to avoid condensation of the water vapor and depletion of the desired volatile organic compounds.

Accordingly, there is a need for an arrangement for the collection and analysis for alveolar breath which avoids the depletion of volatile organic compounds and which does not require heating systems to prevent the condensation of water vapor in the alveolar breath.

SUMMARY OF THE INVENTION

These and other objects of the invention are achieved by an arrangement for collection of alveolar breath into a breath reservoir comprising a hollow container having a first end and a second end, a breath entry portal proximal to the first end, a breath exit portal proximal to the second end, and a sampling portal between the end and exit portal. A condensation unit connected to the sampling portal removes water vapor present in the alveolar breath.

Surprisingly, it has been observed that contrary to the expectations of those skilled in the art, promoting condensation of the water vapor in alveolar breath, rather then depletion, actually results in enhanced concentration of volatile organic compounds in alveolar breath.

DETAILED DESCRIPTION OF THE PREFERRED EMBODIMENTS

Figure 1:
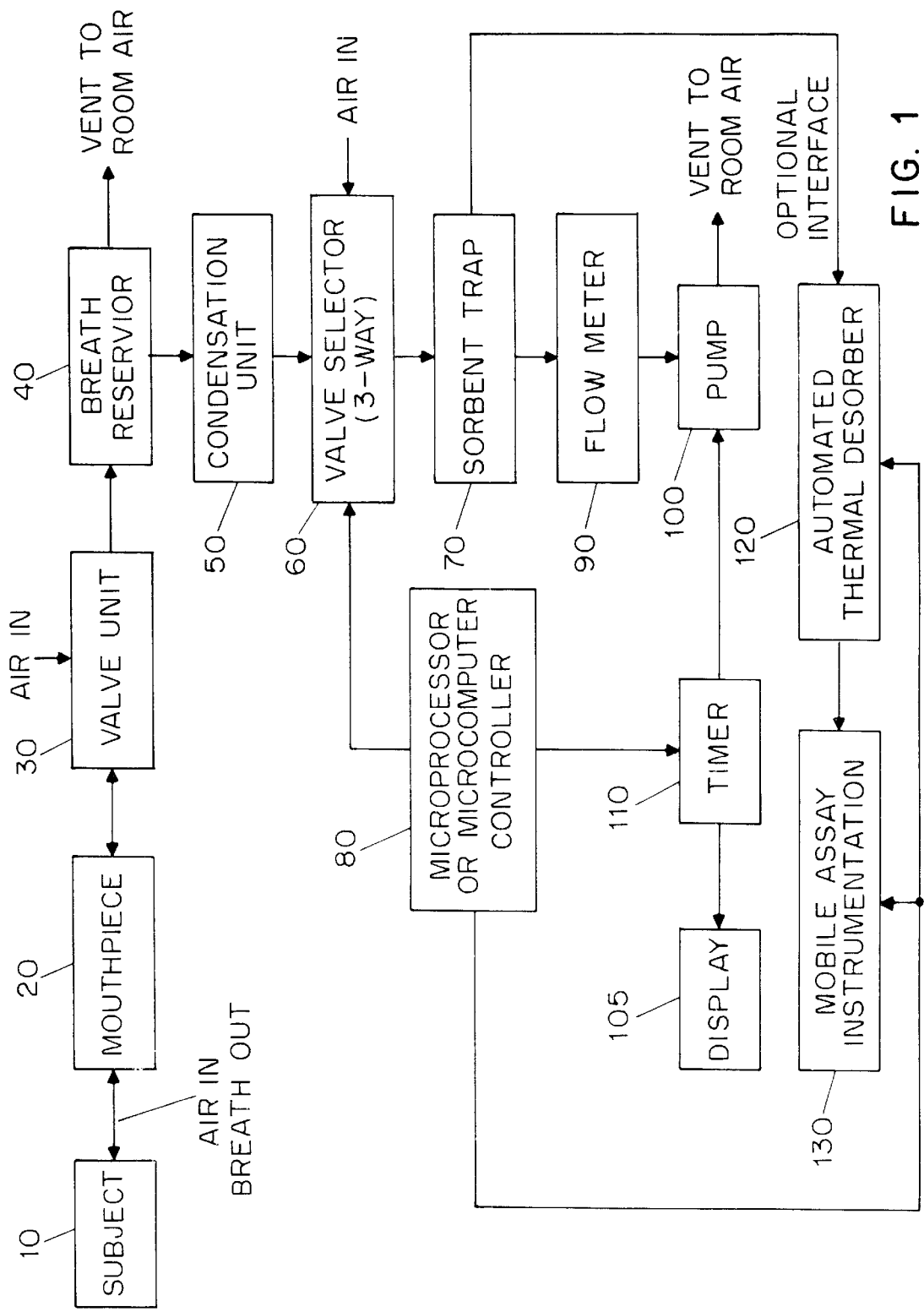
FIG. 1 is a schematic block diagram of an arrangement for the collection and analysis of alveolar breath in accordance with the invention.

A preferred arrangement for the collection of alveolar breath is shown in FIG. 1. A subject 10 blows into a tubular wide-bore mouthpiece 20, approximately one inch in diameter which provides very little resistance to expiration. The exhaled breath is conveyed through valve unit 30 to breath reservoir 40 and to condensation unit 50 where water vapor in the breath is condensed.

The mouthpiece 20 is typically a disposable polycarbonate plastic unit and the valve unit 30 comprises light latex valves. The subject wears a nose clip and breaths in and out through the mouthpiece and valve unit. This ensures that room air is inhaled but all expired breath is transmitted to breath reservoir 40. The low resistance of the valve unit 30 and the breath reservoir 40 open at its distal end ensures that breath samples may be collected without discomfort even from subjects who are elderly, or may be suffering from respiratory disease.

The breath reservoir 40 comprises a metal or plastic tube open at the distal end which allows expired breath to vent to room air. In the embodiment shown in FIG. 1, the breath reservoir 40 includes a tube with an internal diameter of 2.4 cm and a length of 100 cm. The tube is pivotally connected to the valve 30 and mouthpiece 20 so that it can be adjusted to the most comfortable position for the subject donating a breath sample. A single expired breath enters the breath reservoir 40 as a column. The downstream segment of this column, i.e., the segment furthest from the mouth comprises dead space breath from the upper airways, nasalpharynx, trachea and bronchi. The upstream segment of the column, i.e. the segment closest to the mouth, comprises alveolar breath from the lungs. In a normal adult, the volume of a single breath at rest, i.e. a tidal breath, is approximately 500 ml, of which 150 ml is dead space breath and 350 ml is alveolar breath. Breath is conveyed from a sampling port at the proximal end of reservoir 40, closest to the mouth. The importance of this configuration is that the breath sample drawn into the condensation unit 50 is alveolar breath which is virtually uncontaminated by dead space breath. This ensures that the collected sample reflects the abundance of volatile organic components in the pulmonary capillary blood and alveoli where gaseous interchange occurs, not dead space breath. The sampling rate is adjusted such that the column of alveolar breath is not depleted before the arrival of the next breath.

The condensation unit 50 comprises a tube of metal or plastic maintained at room temperature. Suitable plastics include but are not limited to teflon and polycarbonate. Preferably, the tube is approximately 50 cm in length and has a 3 mm ID. The condensation unit 50 depletes the alveolar breath sample of water before it reaches sorbent trap unit 70. Surprisingly, it has been found that the use of condensation unit 50 yields improved capture of volatile organic components in sorbent trap unit 70. While not wishing to be bound by any theory, it is believed that depletion of water from the breath sample results in reduced competition by water for binding sites in sorbent trap unit 70, thereby increasing the capture of breath volatile organic components.

The residual gaseous components, including the volatile organic components of interest are received by valve selector 60 and conveyed to sorbent trap unit 70. A microprocessor 80 controls the valve selector 60 and determines whether the sample flowing to the sorbent trap unit 70 is alveolar breath or ambient room air. Typically, two consecutive samples are collected into separate sorbent traps, one of alveolar breath, the other of room air.

A flow meter 90, pump 100 and timer 110 are adjusted to determine the amount of breath sample delivered to sorbent trap unit 70. Optionally, a display unit 105 can be used to monitor the breath delivery cycle. Typically a flow rate of 0.5 l/min. for a collection period of 2 minutes is employed, resulting in the delivery of 1.0 liters of alveolar breath to the sorbent trap unit 70. This was found to result in virtually no detectable breakthrough of sample from the sorbent trap unit 70. However, larger or smaller samples may be readily collected, depending upon the target analyte in breath under study.

The sorbent trap unit 70 shown in FIG. 1 is a stainless steel tube containing activated carbon. However other sorbent materials or resins, for example Tenax available from Supelco, Inc. located in Bellefonte, Pa., can be employed. A preferred sorbent trap is 200 mg Carbotrap C 20/40 mesh and 200 mg Carbopack B 60/80 mesh available from Supelco, Inc. located in Bellefonte, Pa. In a preferred embodiment the sorbent trap unit 70 includes two traps. One trap is connected to the condensation unit and collects breath volatile organic components. The second trap collects a similar volume of room air. The valve selector unit 70 directs the flow of alveolar breath or room air to their respective sorbent traps.

The volatile organic components captured in the sorbent trap unit may be assayed by removing each sorbent trap in the sorbent trap unit 70 from the arrangement and sending it to a laboratory. In the alternative shown in FIG. 1 the volatile organic components from breath are desorbed from the sorbent trap in unit 70 by an automated thermal desorber 120 which heats the sample. The automated thermal desorber 120 includes a heating unit which heats the sample to 200° C. or higher, and a secondary smaller trap containing sorbent material similar to the sorbent material in sorbent trap unit 70. Upon heating one of the sorbent traps, the volatile organic compounds absorbed into that sorbent trap in the sorbent unit 70 are thermally desorbed, and a stream of inert gas, for example helium or nitrogen is introduced, flushing the desorbed volatile organic components to the secondary smaller trap where the sample is captured and concentrated for subsequent assay.

A mobile assay unit 130 receives the volatile organic components which are desorbed from the secondary smaller trap by heating to 200° C. or higher with the automated thermal desorber 120. The mobile assay unit 130 may comprise one or more of a gas chromatograph, mass spectrometer, infrared spectroscope, or an electronic nose detector to determine the identity and quantity of the volatile organic components. However, any instrument for analysis of volatile organic compounds may be employed. When analysis of the breath volatile organic components is complete, the process is repeated for analysis of the room air volatile organic components contained in the second sorbent trap in the sorbent trap unit 70. Data from both analysis are downloaded from mobile assay instrumentation 130 into microprocessor or microcomputer 80, and the room air background volatile organic components are subtracted from the volatile organic components present in the breath sample analyzed. The concentration of each volatile organic component in breath minus its concentration in room air is the alveolar gradient and can be used for diagnostic purposes.

The microprocessor or microcomputer 80, in addition to controlling valve selector 60, controls the automated thermal desorber 120 and mobile assay unit 130. The microprocessor or microcomputer 80 may also be programmed with algorithms for analysis and interpretation of the data.

Figure 2:
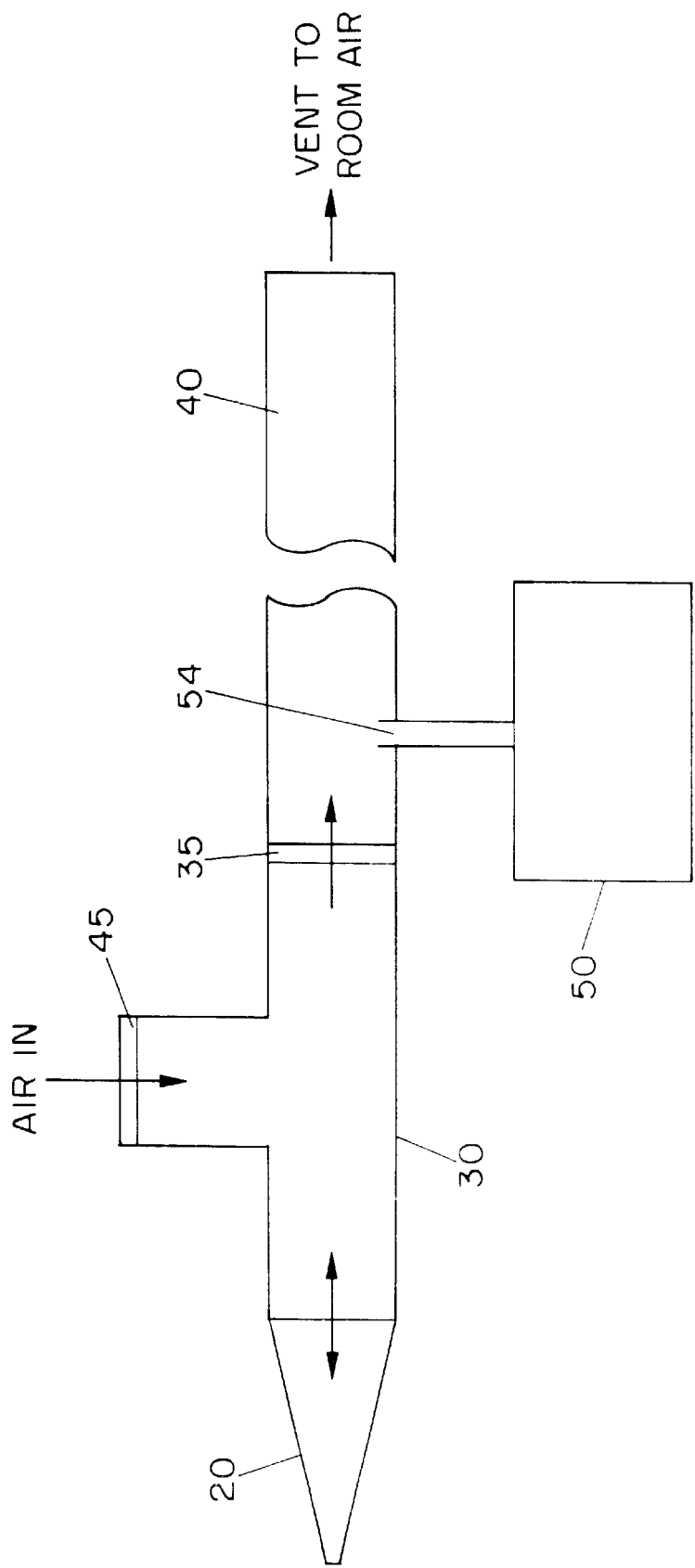
FIG. 2 is a cross sectional illustration, partially in section, of a mouthpiece, valve unit, breath reservoir container and condensation unit in accordance with the invention.

An exploded view of a mouthpiece, valve unit, breath reservoir end condensation unit is shown in FIG. 2. The valve unit 30 is a T shaped connector including latex flap valves 35 and 45 available from Vital Signs, Inc. located in Aurora, Colo. Breath flows from the subject (not shown) through mouthpiece 20 into T shaped valve unit 30 through latex flap valve 35 into the breath reservoir 40 which is vented to the room air. A sampling portal 54 pierces breath reservoir 40 at a point proximal to flap 35 and provides fluid communication between breath reservoir 40 and condensation unit 50.

I claim:

1. Arrangement for collection of volatile organic components in alveolar breath comprising:

a hollow container having a first end and a second end, a breath entry portal proximal to said first end, a breath exit portal proximal to said second end, and a sampling portal between said entry and said exit portals;

a condensation unit downstream from said sampling portal relative to said hollow container, and a sorbent trap downstream from said condensation unit.

2. Arrangement for collection of volatile organic components in alveolar breath according to claim 1 further comprising a coupler which delivers exhaled breath from a subject to the breath entry portal.

3. Arrangement according to claim 1 wherein the sampling portal is proximal to the breath entry portal and distal to the breath exit portal.

4. Arrangement according to claim 1 further comprising a thermal desorption unit connected to the sorbent trap.

5. Arrangement according to claim 4 further comprising a mobile assay unit connected to the sorbent trap.

6. A method for analyzing volatile organic components in alveolar breath comprising:

receiving a breath sample in a breath reservoir, withdrawing alveolar breath from said breath sample, conveying said alveolar breath to a condenser, removing water vapor present in said alveolar breath in said condenser, thereafter contacting said alveolar breath with a sorbent trap, and analyzing volatile organic components absorbed into said sorbent trap from said alveolar breath.

* * * * *

UNITED STATES PATENT AND TRADEMARK OFFICE
CERTIFICATE OF CORRECTION

PATENT NO. : 6,726,637 B2 Page 1 of 1
APPLICATION NO. : 10/008642
DATED : April 27, 2004
INVENTOR(S) : Michael Phillips It is certified that error appears in the above-identified patent and that said Letters Patent is hereby corrected as shown below:

Column 6, line 5, cancel the text beginning with "1. Arrangement for collection" to and ending with "said condensation unit." in column 6, line 14, and insert the following claim:

--1. Arrangement for collection of volatile organic components in alveolar breath comprising:

a hollow container having a first end and a second end, a breath entry portal proximal to said first end, a breath exit portal proximal to said second end, and a sampling portal between said entry and said exit portals;

a passage having a proximal end and a distal end, said proximal end being connected to said sampling portal;

a condensation unit connected to said distal end of said passage, said condensation unit being adapted to deplete an alveolar breath sample of water; and a sorbent trap connected to said condensation unit, said sorbent trap being adapted to capture volatile organic components from a water-depleted alveolar breath sample.--

Signed and Sealed this

Seventh Day of October, 2008

JON W. DUDAS
*Director of the United States Patent and Trademark Office*